United States Patent [19]

Kehr et al.

[11] Patent Number: 5,200,891

[45] Date of Patent: Apr. 6, 1993

[54] ELECTRONIC MEDICATION DISPENSING METHOD

[75] Inventors: Bruce A. Kehr, 9429 Holbrook La., Potomac, Md. 20854; David Lerner, New York, N.Y.; Richard D. Demenus, New York, N.Y.; Michael J. Edl, New York, N.Y.

[73] Assignee: Bruce A. Kehr

[21] Appl. No.: 464,877

[22] Filed: Jan. 17, 1990

[51] Int. Cl.⁵ .................................. G06F 15/42
[52] U.S. Cl. ........................... 364/413.01; 221/2; 221/15; 368/10
[58] Field of Search ............. 364/400, 401, 413.01, 364/479; 221/2, 15, 99; 368/10, 41; 340/309.15, 309.4

[56] References Cited

U.S. PATENT DOCUMENTS

| | | | |
|---|---|---|---|
| 3,966,086 | 6/1976 | Kelso | 221/234 |
| 4,186,438 | 1/1980 | Benson | 395/600 |
| 4,223,801 | 9/1980 | Carlson | 221/3 |
| 4,258,354 | 3/1981 | Carmon et al. | 340/309.4 |
| 4,275,384 | 6/1981 | Hicks et al. | 340/309.4 |
| 4,293,845 | 10/1981 | Villa-Real | 340/309.3 |
| 4,360,125 | 11/1982 | Martindale et al. | 221/2 |
| 4,361,408 | 11/1982 | Wirtschafter | 368/10 |
| 4,382,688 | 5/1983 | Machamer | 368/10 |
| 4,473,884 | 9/1984 | Behl | 364/479 |
| 4,483,626 | 11/1984 | Noble | 368/10 |
| 4,490,711 | 12/1984 | Johnston | 340/309.4 |
| 4,588,303 | 5/1986 | Wirtschafter et al. | 368/10 |
| 4,626,105 | 12/1986 | Miller | 368/10 |
| 4,682,299 | 7/1987 | McIntosh et al. | 364/569 |
| 4,695,954 | 9/1987 | Rose et al. | 364/479 |
| 4,717,042 | 1/1988 | McLaughlin | 221/3 |
| 4,725,999 | 2/1988 | Tate | 368/10 |
| 4,768,176 | 8/1988 | Kehr et al. | 368/10 |
| 4,768,177 | 8/1988 | Kehr et al. | 368/10 |
| 4,837,719 | 6/1989 | McIntosh et al. | 364/569 |
| 4,862,431 | 8/1989 | Drouin | 368/10 |
| 4,879,699 | 11/1989 | Sakamoto | 368/63 |
| 4,926,572 | 5/1990 | Holmes | 40/448 |
| 4,962,491 | 10/1990 | Schaeffer | 368/21 |
| 5,020,037 | 5/1991 | Raven | 368/10 |
| 5,097,429 | 3/1992 | Wood et al. | 364/569 |

Primary Examiner—Roy N. Envall, Jr.
Assistant Examiner—David M. Huntley
Attorney, Agent, or Firm—William D. Hall

[57] ABSTRACT

A device for monitoring medication of a patient and for prompting the patient into certain medication taking schedule and/or certain programming steps and routines. The device has a plurality of compartments, each of which may store medication and an electrical signaling system to emit medication alert signals from time-to-time, each of which the signals indicates (a) that medication should be taken, (b) from which compartment the medication should be taken, (c) and the quantity of medication to be taken. If a designated compartment is not opened and closed within a predetermined period of time, the electrical signaling system will sound an alarm. If each designated compartment is opened and closed, the take-medication signal and the alarm (if operating) are turned off and the event is recorded for later review. The device includes a display having a substantially continuous display area having portions thereof closely adjacent to each compartment.

19 Claims, 12 Drawing Sheets

Last      Fig. 7

Next      Fig. 8

ELECTRONIC MEDICATION DISPENSING METHOD

BACKGROUND OF THE INVENTION

The prior art discloses a number of devices that use electronic systems for assisting a person who takes medication. Kehr U.S. Pat. No. 4,768,177 discloses a device for alerting a person when medication should be taken as well as how much medication should be taken. The Kehr et al. apparatus also has a night cut-off control which permits the device to be turned off at night. Several patents teach the use of a micro-processor to alert a person to take medication and to also supply information for a display of, or a printout of, information about the patient and/or his or her medication; see for example, McIntosh, et al. U.S. Pat. No. 4,682,299, Villa-Real U.S. Pat. No. 4,293,845 and Biehl U.S. Pat. No. 4,473,884.

SUMMARY OF THE INVENTION

The prior art lacks certain features embodied in the present invention, including, but not limited to: a high degree of inter-action between the patient and the messages that the device displays, alerting the patient how to program the device and how to take medications; giving the patient extensive commands in writing; ease of programming and ease of use in a design that is resistent to wear and tear; specific displays to increase the accuracy of programming and pill taking; means to translate routine doctor's orders into standard alarm prompting sequences; first prompting, then recording the patient's behaviors relative to pill taking; and other means, herein specified, that enhance accurate medication in accordance with research studies such as "Patient Adherence to Prescribed Therapies," Marshall H. Becker, Ph.D., Medical Care, Ma 1985, Vol. 23, No. 5.

The present invention is a medication monitoring device which provides a number of functions for facilitating patient adherence to prescribed therapies. The device is capable of accepting, storing and displaying a medication signal as well as physician's instructions, and is capable of monitoring the presumed adherence to the schedule and the instructions.

The device of the present invention provides for ease of entry of a medication schedule, ease of review of that schedule, both prospectively and retrospectively, and allows the patient and/or the physician to readily and accurately review the compliance with that schedule. The monitoring device of the present invention, while providing visually readable instructions, insures that the patient has a correct understanding of the medication regime. Through regular interaction with the patient by its series of medication alert signals, the monitoring device of the present invention reduces the complexity of the medication regime for the patient. The monitor also requires the interaction of the patient through its series of prompts, ques, queries and requests for acknowledgement, thereby engaging the patient as an active participant in the treatment process, enhancing the efficacy of the medication regime.

The device has a plurality of medication compartments in which are inserted a plurality of drawers which may each be used to store a different medication, a microprocessor with associated circuitry for providing timing and signaling, and a display and push buttons for programming and operating the device. The device provides visual signals to prompt the user during input of a medication schedule or schedules. The device then relies upon that schedule(s) to indicate to the user when medication is to be taken by providing audible and/or visual medication alert signals. The device indicates the compartment of the device from which the medication is to be taken and the quantity of medication. The compartment indication is provided by illuminating a light closely associated with the desired compartment. A liquid crystal or other type of display indicates the quantity to take; i.e. if three pills are to be taken, the number "3" will be displayed adjacent to the appropriate compartment.

If the patient obeys the commands of the system and opens the designated compartment, the signals and lights will be turned off until the next medication alert time arrives. The unit can optionally be designed to turn off the alert after the drawer is closed. The drawers, as well as the sides or bottoms of the compartments, may be made transparent in order to allow the user to visually check if any pills are in the compartment and to determine the type of medication, if any is present. The drawers, when opened, reveal their entire length, and have a sloped front, allowing easy access for the patient who may have tremor, arthritis or other difficulties.

If the patient fails to obey the commands of the system and does not open and close each designated compartment within a predetermined interval of time, the audible signal will continue at predetermined periodic intervals, and a visual indication will be provided (e.g. "MISSED MEDICATION"), informing the patient that he forgot to access the appropriate compartment(s), which compartment(s) he forgot to access, and how much medication he forgot to take. The visual alarm and the lights will then be shut off when the designated compartment is opened (or, optionally, opened and closed). The patient may also indicate to the unit that he will be skipping that medication, and the alarm will be cleared.

Generally, any single medication is to be taken periodically throughout the day. The most common schedules will be available within the unit for selection by the user (e.g. once every other day, once per day, twice per day, three times per day, four times per day). The user must also provide a first dose time. If, for example, the user selects "four times per day", the first alarm will sound at the user selected first dose time, and three subsequent alarms will sound at each four hour interval thereafter. This is in accord with standard prescription labeling and standard dispensing routines. The user may change the first dose time at will, and all alarms scheduled in this manner will be shifted to match the new first dose time.

Each compartment may be independently set for one of these standard schedules, or the patient may enter a "special" schedule of up to 12 specific clock times per day that pills should be taken from a given compartment. In this manner, the most common schedules may be set very simply, but the unit is flexible enough to accommodate patients with more complex requirements.

By providing built-in programming which understands the multiple times per day format, the device automatically displays doctor's instructions and translates these into specific pill-taking times and quantity indications. This is accomplished in that the user only needs to enter the instructions as written by the doctor, e.g. "three pills four times per day," confirm the display of this information and specify a given compartment. The device then automatically, in conformance with its built-in program, translates this into a set of medication alarms such as 8:00 AM, Noon, 4:00 PM and 8:00 PM. The device also allows for specific programming of pills which need to be taken with meals or at bedtime by allowing the user to program in the patient's usual mealtimes or bedtime, the device can then be instructed to alert for a desired medication at those programmed meal and/or bedtimes. The device also provides for tables against each compartment specifying the doctors instructions so that the display for a specific compartment can be compared to the information on the respective label.

The use of a LCD screen allows the patient to be visually prompted during both the programming operation and the medication alert operation of the device. The built-in programming of the device also accommodates a number of confirmation steps, allowing the patient or user to doublecheck the entries before they are stored into the device which provides for more accurate medication monitoring. The many programmable schedule options of the device allow for instructions for "every other day" medication in addition to multiple medication on a given day.

The prompt-then-record system, is taught by the monitor of the present invention. Here the device does hot record an instruction until it is confirmed; and requires a response or acknowledgement to a prompt, (such as a medication alert) prior to recordation so that the event may be recorded as an "acknowledged" or "unacknowledged" event to indicate pills taken or missed, thereby increasing the accuracy of the medication monitoring. The prompt-then-record can also be utilized to record and indicate other abnormalities in the medication schedule.

The device has a number of manually operable switches or buttons that are used to set proper operating conditions, and to interact with the device during it's operation. The user is prompted by words and phrases, on the built-in display, to simplify setting of the device. The embodiment of the invention illustrated and described herein includes user-input buttons on the front panel of the device adjacent the display. The first two buttons of the display are the "Next" and "Last" buttons, described in more detail below, which allow prospective and retrospective review of the medication schedule, respectively. These buttons also allow cycling forward or backward through the different options in the various programs available within the device, such as the time of day options described above. The buttons are arranged closely adjacent one another so that the user can readily identify their similar functionality and can readily switch forward and backward between the options of the given programming mode. Providing the "Next" and "Last" buttons allows ease of programming over devices which simply provide for a common mode cycling button, while allowing for simplified design over devices which require multiple buttons, each for a specific task. The patient can readily master the next/last sequencing logic which carries throughout the various programming modes where these buttons are utilized in a common manner.

The next group of buttons is the "Check and Set" buttons. The "Check" button allows cycling between the different modes of the apparatus, e.g., time of day, first dose time, compartment scheduling, etc. The "Set" button allows the patient or user to enter one of these programming modes and then alter the programming within the mode. By closely associating these two buttons, the patient or user readily becomes familiar with their interaction and therefore, the programming is made more easily accessible.

The last set of buttons is the "Yes/Okay" and "No" buttons. These buttons are utilized by the patient to answer queries' or provide acknowledgements. As these buttons are similar in their functioning and there is interplay between their applicability, they have been grouped together to provide easier user mastering of the utilization of the device.

A final button, the "no-bell" button, allows the patient to suspend the audible tone for predetermined time periods.

As stated above, the visual and audible medication alert signals, are turned off when the patient opens the compartment. This operation is carried out by having a separate closure (for example a lid) for opening and closing each compartment or by providing drawers within each compartment which slide out for access. When the lid or drawer is moved to open the compartment, a switch operating through the electrical circuitry of the signaling system, turns off the visual medication alert signal and/or the audible alarm.

The electronic circuitry of the unit may be realized in many ways. One embodiment using a 4-bit microcontroller integrated circuit, the Hitachi HD407L4808, and some associated components, such as light emitting diodes (LEDs), a liquid crystal display (LCD), resistors, capacitors, batteries, etc., is illustrated herein.

The microcontroller continually operates in a low power mode with a 32 kHz clock crystal, and each half second an interrupt is generated to change the state of the colon (such that the colon is continually blinking, on for one half second and then off for one half second), incrementing the time keeping circuitry and keeping track of the time of day. The time of day may be shown on the unit's display. The time of day is continually compared against the scheduled medication times, and, when a match is found, an output of the microcontroller is enabled to turn on the light associated with the appropriate compartment, and other outputs are set to enable the audible signal and to show the number of pills on the display associated with that compartment.

The opening and closing of the various compartments is sensed by the microprocessor through the actuation of individual switches associated with each compartment. Each medication alert and associated taking or skipping of medication is stored in the microcontroller's random access memory (RAM), so that the patient can later review when and if pills were presumably taken or skipped.

If desired, the audible signal may include the use of a transducer which emits speech giving special instructions to the patient relating to the taking of the medication.

By pushing a single button, the patient may, at any time, examine the schedule of medications to be taken over the next period (e.g., 24 hours). By pressing another button, the patient may review the actual times that doors were opened (and medication presumably taken) over the previous period (e.g. 24 hours). The memory storing the prospective and retrospective information may be extended, by use of additional RAM, to provide a longer time period for review, and an electronic output may be provided so this information can be directly transferred to a computer or to a printer for analysis by a pharmacist, physician, family member or other interested party.

If a compartment is opened when no pill is scheduled, the unit "chirps", and displays a question to the patient to determine if he is taking an unscheduled pill, in order to prevent the unit from recording that a pill was taken when a patient merely opens a door to check the pills or to refill a compartment. If the patient responds negatively or does not respond at all, the compartment opening is not recorded and the device assumes that the compartment was opened for checking or refill. The unscheduled pill taking is recorded in the unit's memory only if the patient responds positively.

The unit can also include a plurality of other user input buttons arranged so that buttons are grouped according to common function. This allows the user to readily identify related buttons for desired sequencing.

During programming, the unit can also display specific doctors orders on the LCD and query the patient as to whether what the patient is programming in conformance with those orders.

The unit can also display a specified medication identification on the LCD for the user to compare against the medication bottle, or label on the medication compartment, and indicate if it is the same by supplying a "YES/OKAY" or "NO" answer to the device. If the user selects "YES," the identification is stored. If "NO," the display is altered until the desired identification is displayed.

By pushing a button, the patient can suspend the audible alarm. Each push of the button suspends the audible alarm for a predetermined time period (e.g. one hour). The LCD displays a symbol that indicates that the audible tone has been suspended, while the visual alarms and prompts continue to operate as programmed. If the patient is going into a concert or meeting and does not want the device to interrupt, he can suspend the audible alarm. When he leaves the concert and references the device, it will indicate the type and quantity of medication missed and when it was scheduled, via the visual means which was not suspended.

The volume of the audible tone can also be programmed in by the patient to suit their wishes.

One button allows the patient to review and display what has been programmed into the device. With any display then showing, the push of a second button allows the device to enter the "programming mode" wherein the particular program displayed can be altered through the push of other buttons. In this programming mode, the device queries the patient as to whether each new program displayed is "OKAY," and patient can indicate "YES/OKAY" or "NO". "YES/OKAY" enters the new program into the device. Pressing "no" allows the patient to push buttons to display yet a different program on the device, until the correct program is displayed, wherein the pressing of the "yes/okay" button then locks in the correct program into the device. This sequential pushing of buttons to reprogram the device helps to prevent inadvertent alteration of the programming (e.g. through buttons being pushed by a child or inadvertently pushed when the device is placed in a handbag).

At any time if the programming routine is interrupted for more than one minute, or if buttons are pushed inadvertently, the device will automatically return to "time of day," and the interrupted programming will not be entered, as the user did not press the "YES/OKAY" button.

A "low battery" prompt appears when it is time to change batteries. When batteries are removed for changing, the device retains its programming for several minutes.

To help extend battery life, the audible tone beeps only once at alarm time; if the patient does not access the appropriate drawer within one minute, the tone then beeps for an extended ten seconds as a longer reminder to the patient; if patient still doesn't access the appropriate compartment, the unit beeps once every five minutes. Until the appropriate compartment is accessed by the patient; or until the next alarm cycle for that compartment, the device will continue to instruct the patient by displaying the LCD quantity indicator and flashing the LCD over the appropriate compartment(s).

BRIEF DESCRIPTION OF THE DRAWINGS

For a better understanding of the nature of the present invention, reference is had to the following figures and detailed description, wherein like elements are accorded like reference numerals, and wherein.

DETAILED DESCRIPTION OF AN EXEMPLARY EMBODIMENT

Figure 1:
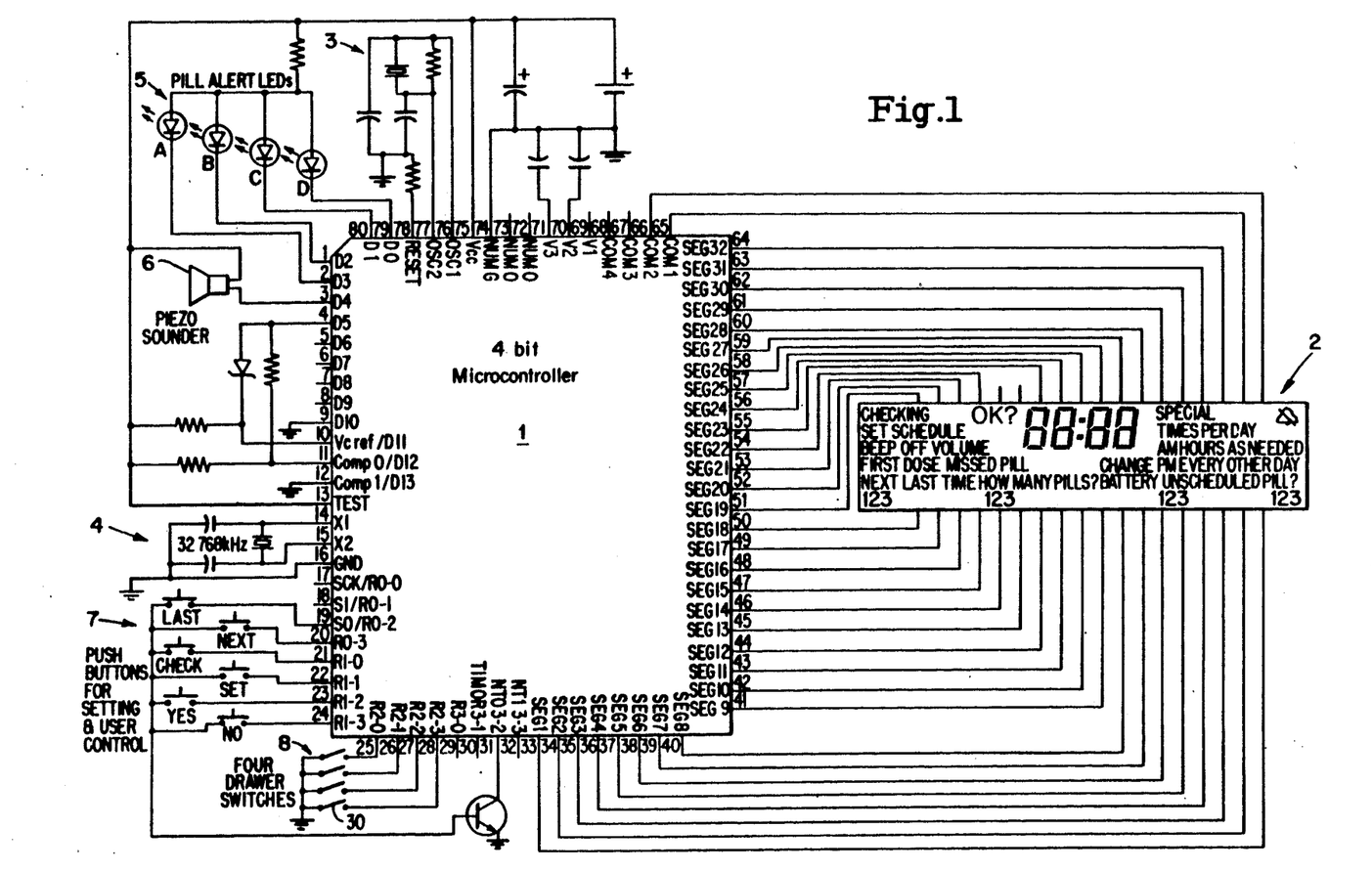
FIG. 1 is a circuit diagram of the medical monitoring device.

As illustrated in FIG. 1, the present invention utilizes an Hitachi Model HD4074808 microcontroller chip 1 for accepting user inputs and for performing the necessary logic for driving the liquid crystal display 2 and associated medication alert signals.

The microcontroller 1 is a MCU microcomputer utilizing a 4-bit architecture and having built-in ROM and RAM. The chip includes a 16 digit LCD driver and 30 I/O pins. The microcontroller 1 is also provided with a crystal oscillator circuit 3 for supplying the internal clock and timing circuits for proper operation of the microprocessor 1. The chip is also provided with a clock crystal circuit 4 to enable the chip to accurately track the time of day in order to display the necessary medication alerts at the appropriate times.

In addition to the liquid crystal display 2, a series of light-emitting diodes (LEDs) A-D are provided in circuit 5, which, along with Piezo buzzer 6 are, attached to I/O ports of the microcontroller 1. A series of push buttons 7, as well as a series of drawer switches 8, are connected to the 4-bit I/O ports of microcontroller 1. The liquid crystal display 2 is attached to the segment driver pins of the microcontroller 1.

Figure 3:
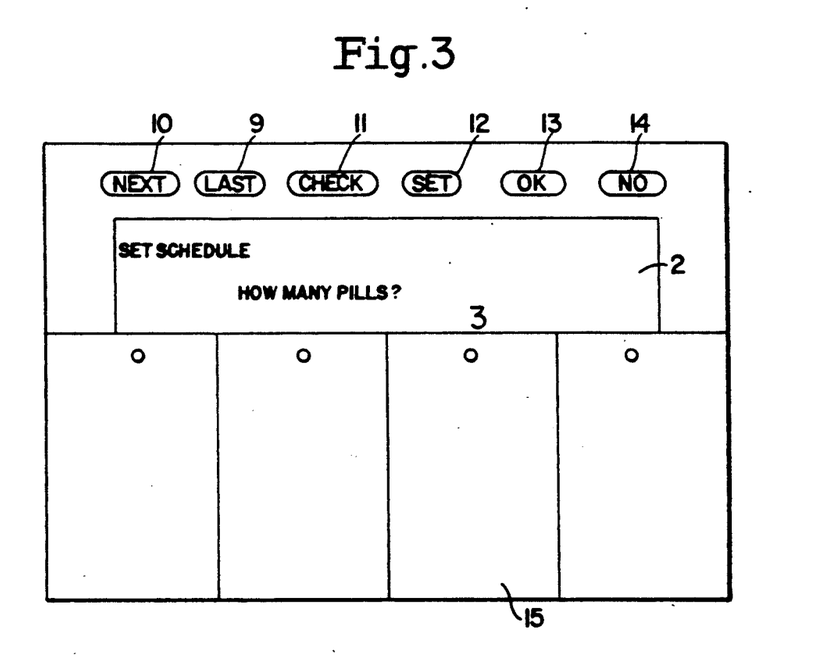
FIG. 3 is a top view of the device with the liquid crystal display illustrating one step of one of the programming modes of operation.
Figure 4:
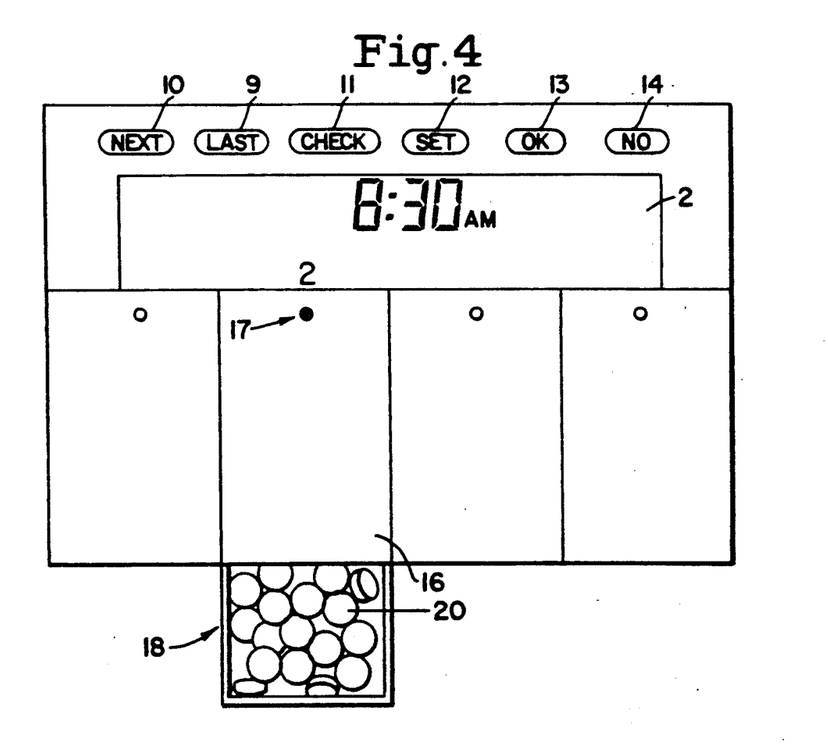
FIG. 4 is a top view of the device with the liquid crystal display indicating the time of day and displaying a pill-taking prompt.

The pill box itself, as illustrated in FIGS. 3 and 4, has a top face on which is positioned the LCD display 2 as well as push buttons 9, 10, 11, 12, 13 and 14. During programming, the LCD display will display a variety of messages. One set of messages is utilized to prompt the user into providing appropriate information to the microprocessor 1. This information is needed by the monitor to establish the appropriate medication schedule. FIG. 3 illustrates an example of the monitor displaying a request for user inputs in the "set schedule" mode displaying the prompt "How many pills?" to request a pill number input from the user.

The pill number "3" is also currently displayed above the third pill box compartment 15, indicating a response from the user. If this setting were accepted, that would instruct the monitor to remind the user to take three pills from compartment 15 at a designated time. As discussed in greater detail below, the number of pills, the medication alert time and the designated compartment can be selected through the operation of push buttons 9-14.

In FIG. 4, the time of day is displayed on the LCD display 2 as well as a digit "2" above compartment 16. Further, the LED 17 associated with compartment 16 is actuated. This combination of an actuated LED 17 and a display of a digit "2" is an indication to the user that two pills should be taken from the drawer 18 located within compartment 16. The drawer 18 is illustrated in the open position exposing pills 20 therein so that they may be taken by the user.

Figure 2A:
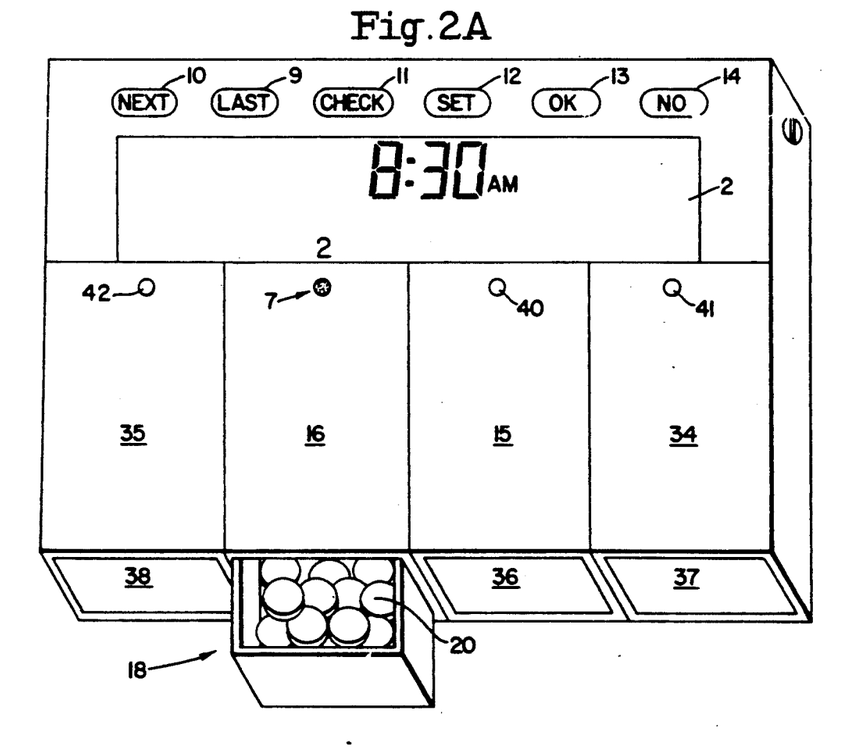
FIGS. 2A and B are a perspective views of the monitoring device.
Figure 2B:
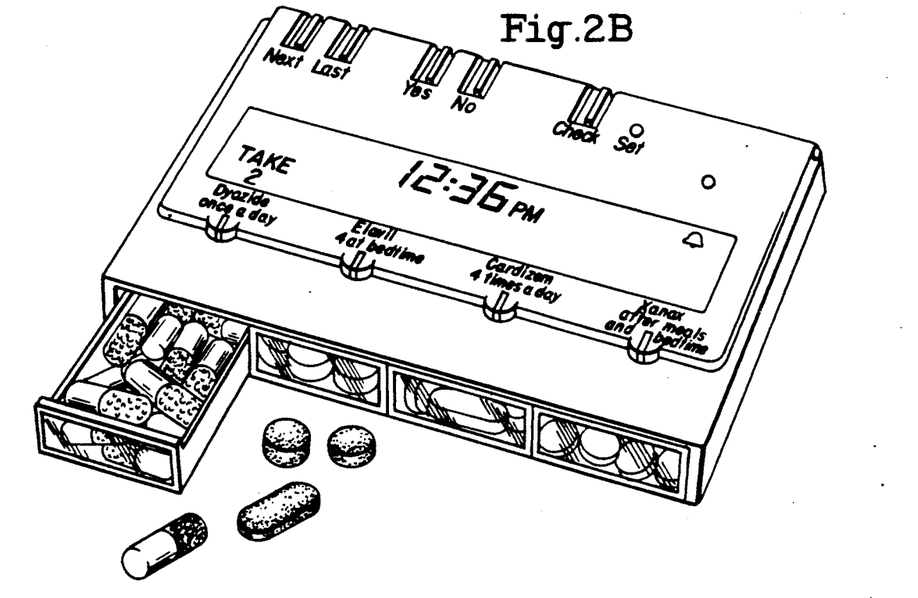

FIG. 2 illustrates an exemplary embodiment of the monitor with four compartments 16, 15, 34 and 35, each compartment having a drawer 20, 36, 37, 38 and an LED 17, 40, 41, 42 respectively. The user is prompted to open a designated drawer in a designated compartment by activation of the LED corresponding to the appropriate compartment.

Figure 5A:
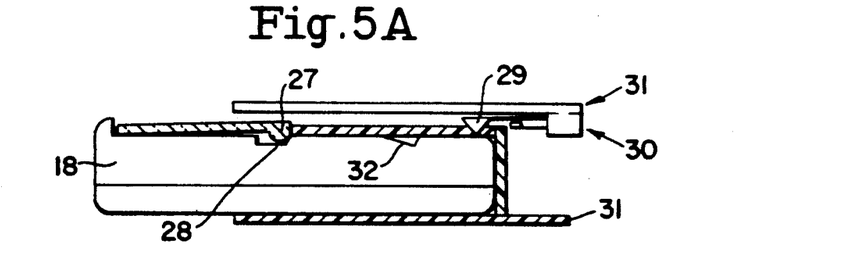
FIGS. 5A-5D are side cross sectional views illustrating one pill compartment of the device.

FIGS. 5A-5D illustrate the opening and switch actuation mechanism of the drawers. When drawer 18 is closed, as illustrated in FIG. 5A, a detente arm 27 attached to compartment 16 is engaged in the detente notch 28 in drawer 18. The detente restraint pressure is easily overcome by slight pulling force on the drawer 18. As drawer 18 is opened, plunger 29 of microswitch 30 mounted on the housing 31 drops thereby closing microswitch 30. Microswitch 30, illustrated in FIG. 1 as part of the drawer switch circuitry 8, when closed grounds terminal R2-1. The grounding of the particular terminal associated with a particular drawer provides a signal to the microprocessor to deactivate the current medication alert which is associated with that drawer.

Figure 5B:
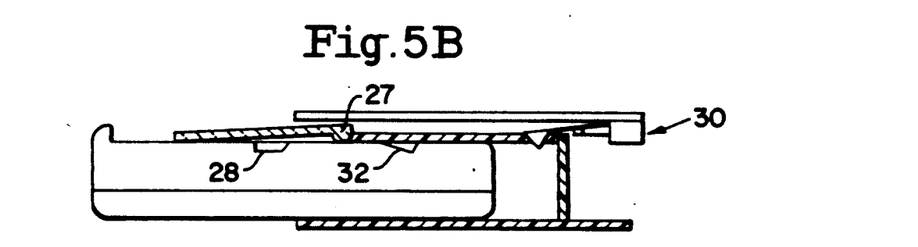
Figure 5C:
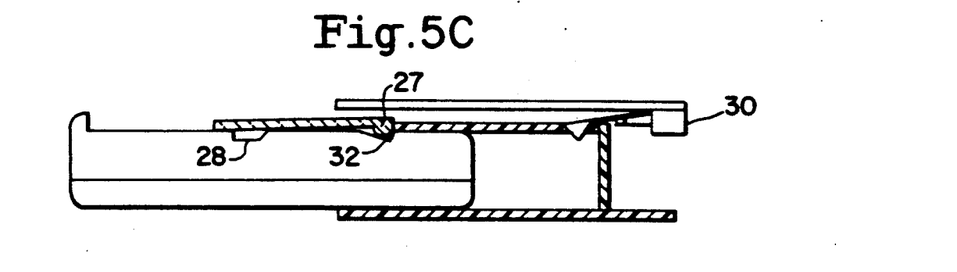
Figure 5D:
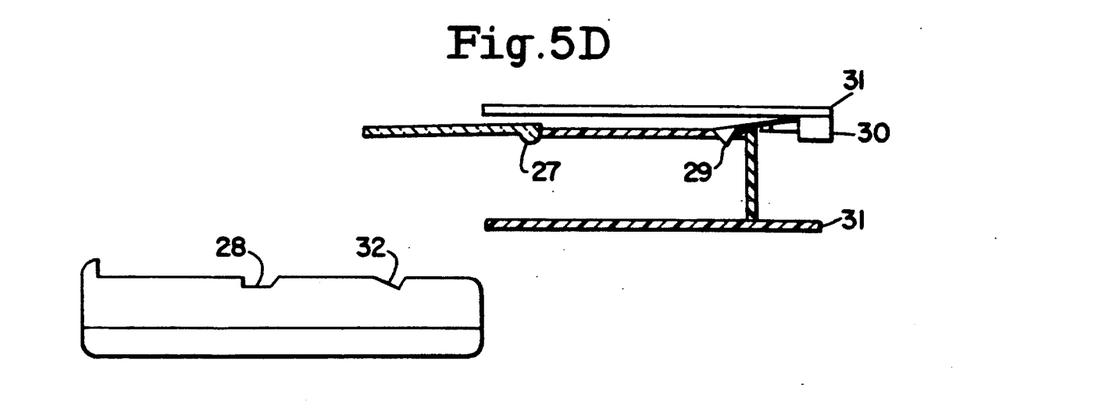

As the drawer is further slid open, as illustrated in FIG. 5C, the detente arm 27 lodges in second notch 32 of drawer 18. The lodging of detente 27 in second notch 32 holds the drawer in an open position in order to facilitate pill removal. The drawer 18 can be completely removed from the housing 31, as illustrated in FIG. 5D, for refill, cleaning or other purposes.

When drawer 18 is pushed back to its closed position, post 29 of microswitch 30 will be deflected thereby reopening microswitch 30. The reopening of microswitch 30 provides a signal to microcontroller 1 to indicating that the drawer has been closed.

When the compartment 18 is open and switch 30 closed, the microprocessor 1 is instructed to discontinue the medication alert signal such as that illustrated in FIG. 4. The time at which the switch 30 was closed, indicating the opening of the compartment 18, is stored in the microcontroller's random access memory (RAM). Each time the drawer is opened, the time of opening and the particular drawer opened is recorded in the microcontroller's RAM. If a take medication signal is generated and the corresponding drawer is not opened at that time or within a predetermined time period thereafter, this is also stored in the microcontroller's RAM as a missed pill event, along with an indication of time and the number of pills that should have been taken, with an indication that the corresponding drawer was not opened at that time. All of this information is stored in the RAM so that it can later be accessed by the user to review the taking of medication and the missing of medication.

The microcontroller 1 keeps track of time and updates the time of day display on the LCD display unit 2. The current time of day of the microprocessor 1 is continually compared against the stored times for scheduled medication. When this comparison generates a match between the stored scheduled medication times and the actual time of day, the microcontroller 1 enables one of the output terminals to the appropriate LED of the LED set 5. Simultaneously, the corresponding segment driver outputs are enabled to indicate the number of pills that should be taken from the designated compartment at that medication time. Further, if enabled by the user, the audible alarm is also triggered.

Figure 6:
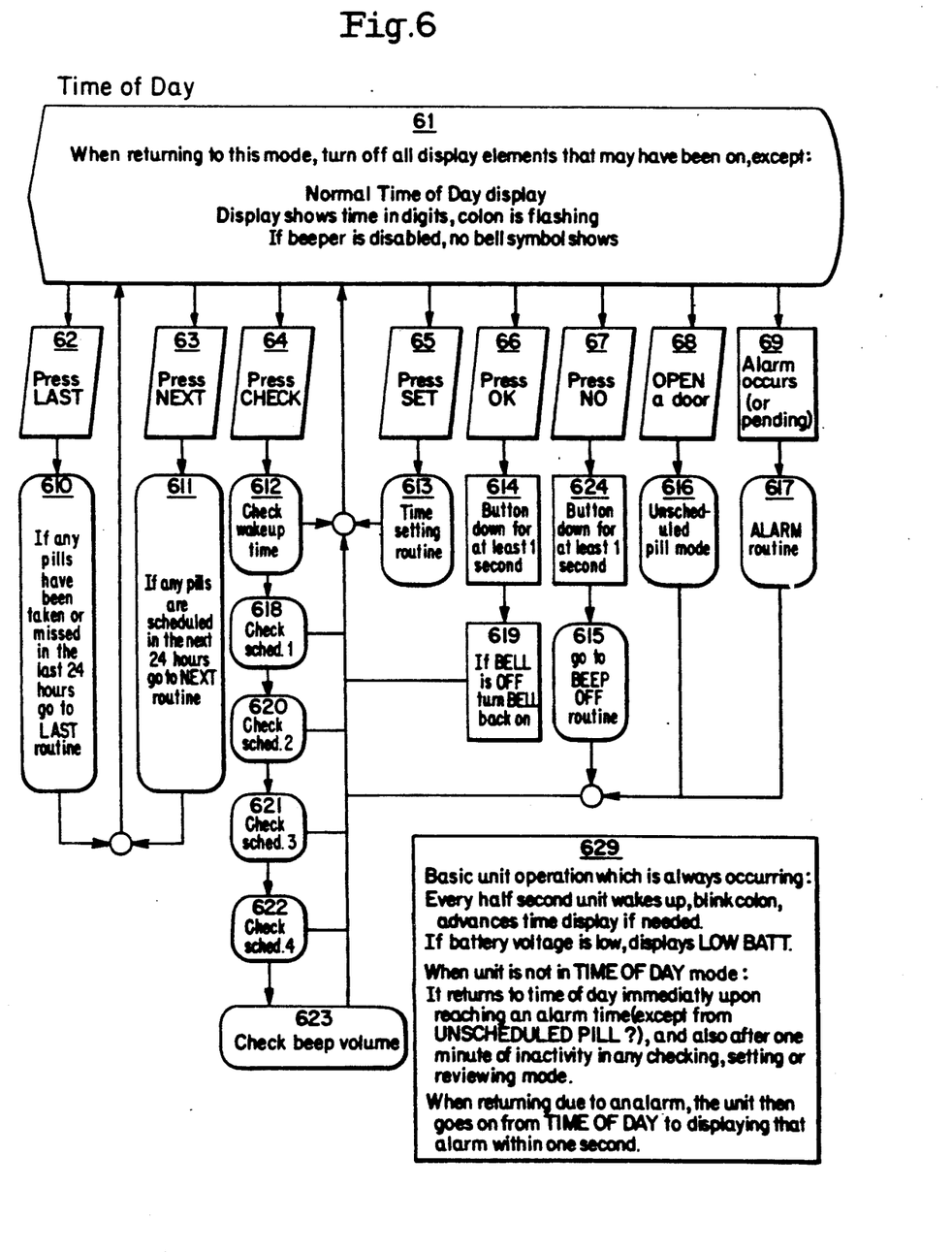
FIGS. 6-16 are logical flow diagrams illustrating the logical operation of the medical monitor device of the present invention.

The logical operation of the microcontroller will now be described with reference to FIGS. 6-16. FIG. 6 is an over view of the logical operation of the various monitoring routines of the monitor. Block 61 of FIG. 6 illustrates the standard resting or time-of-day mode for the microprocessor operation. This is the mode to which the microprocessor returns when no other function is being performed. In this mode, the liquid crystal display 2 displays the time of day and a flashing ":" to indicate that the monitor is operating. Blocks 62-68 illustrate the various user inputs which can be detected by the microprocessor. Blocks 62-67 correspond to the push buttons 9-14, respectively, which are illustrated in FIGS. 2, 3 and 4 on the top of the monitor housing. Blocks 68 and 69 correspond to the input received when a drawer is opened or when a scheduled time is reached, respectively.

Figure 11:
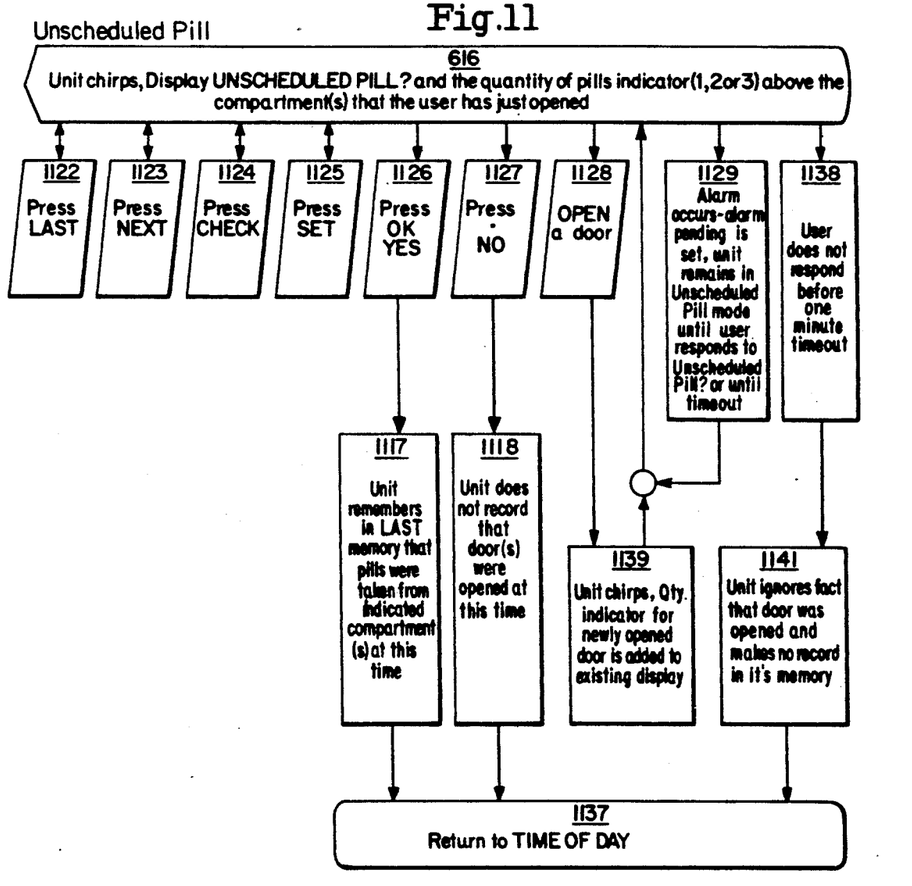

If a drawer is opened while the microprocessor 1 is in this mode, as illustrated by block 68, the microprocessor will jump to the unscheduled pill routine designated by block 616 and further detailed in FIG. 11.

Figure 12:
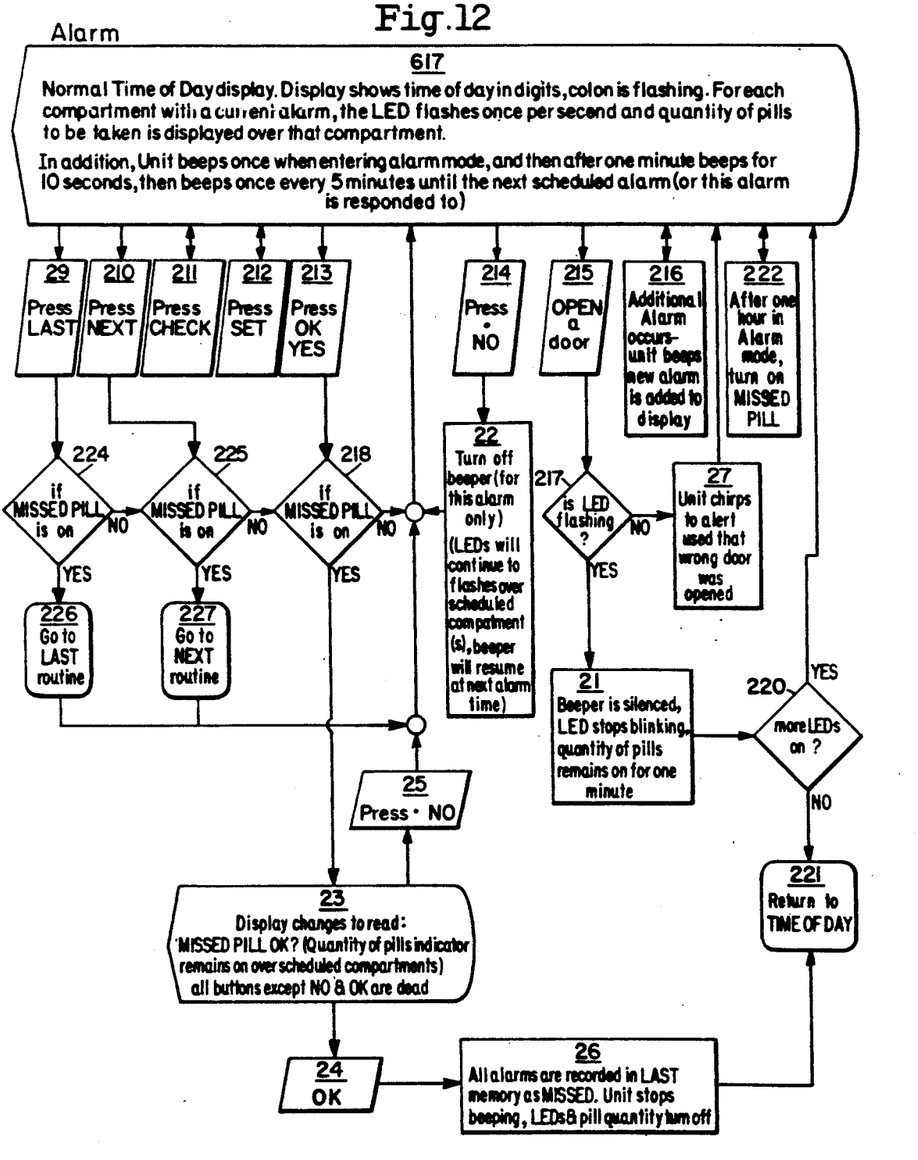

If an alarm occurs or is presently pending, as illustrated by block 69, the microprocessor 1 will jump to the routine illustrated by block 617 and further detailed in FIG. 12. The alarm routine is, therefore, entered through the internal generation of the correspondence between a scheduled medication time and the current time of day of the microprocessor 1. The unscheduled pill routine is entered through the enabling of one of the inputs connected to the drawer switch circuitry 8 as illustrated in FIG. 1. This occurs when a drawer is open and the corresponding switch is triggered without the user first being prompted by the occurrence of a scheduled medication alert through the running of the alarm routine.

Actuating one of the user input buttons 9-14, will cause the microprocessor 1 to enter the appropriate corresponding routine. Actuating the "YES/OKAY" button 13, as illustrated by 66, and maintaining the button actuated for at least one second will cause the audible alarm to be reactivated if it has been suspended. Maintained actuation of the "NO" button, as illustrated by blocks 67 and 624, will cause the audible alarm to be deactivated. Actuation of the "set" button 12, as illustrated by block 65, will cause the microprocessor 1 to enter the time setting routine better illustrated in FIG. 10. Once the time setting routine has been completed, the microprocessor 1 will return to the time of day display mode as described above.

Figure 7:
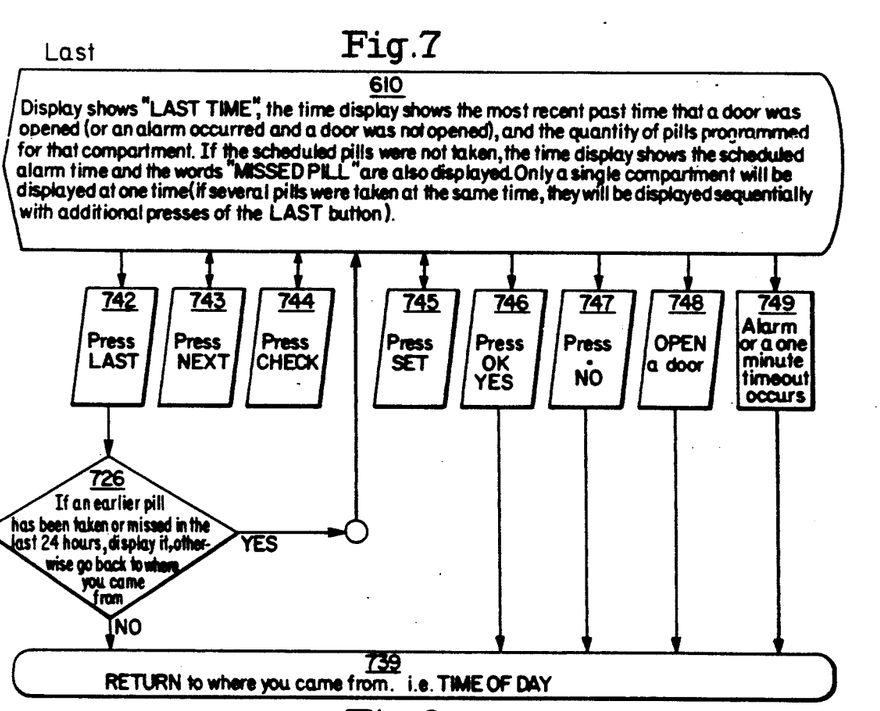
Figure 8:
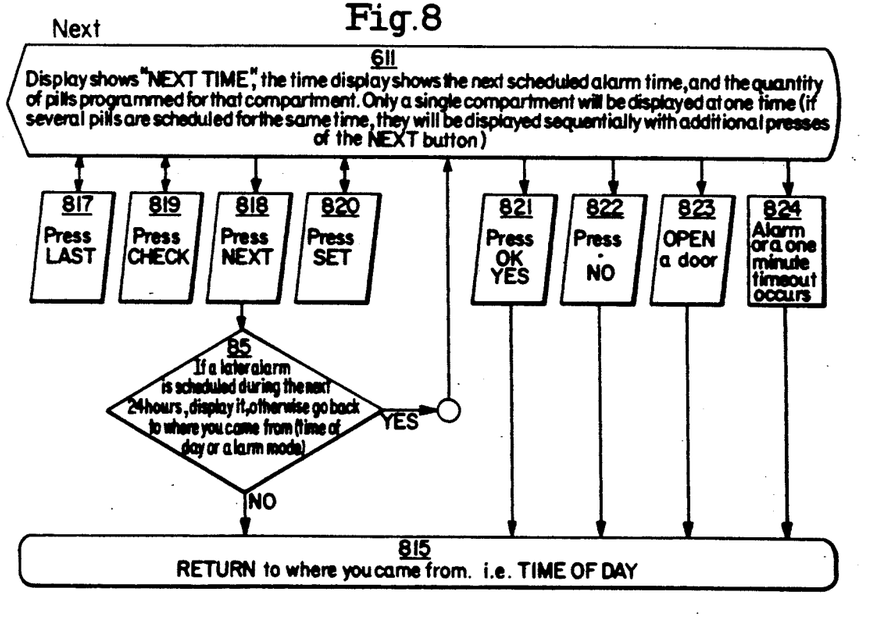

Actuating the "LAST" button 9 or the "NEXT" button 10 will cause the microprocessor to display the last 24 hours of access to the drawers including; medication taken on schedule, missed medication, and unscheduled compartment openings; or the next 24 hours of scheduled medication, respectively, by entering the last routine, FIG. 7, or the next routine, FIG. 8, respectively.

Figure 9:
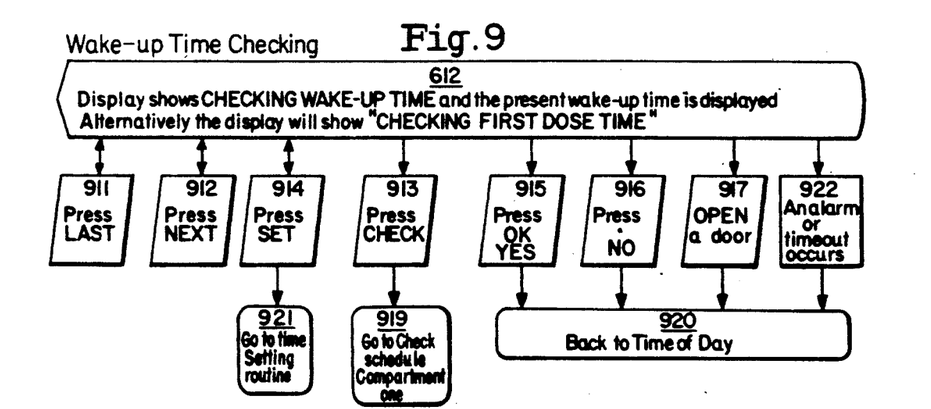

Actuation of the "CHECK" button 11 will cause the microprocessor 1 to go into the First-Dose-Time routine as illustrated by block 612 and in greater detail in FIG. 9. As illustrated in both FIGS. 6 and 9, the user can elect to go to the check schedule routine, block 618, or to return to the time of day display. The check schedule routine, illustrated in detail in FIG. 13, allows the user to check the scheduling stored in the microprocessor 1. It also enables user to cycle through checking "BEEP VOLUME," "BEEP OFF" number of hours, and "TIME OF DAY".

When in the "LAST" routine, as illustrated in FIG. 7, the display 2 initially indicates the most recent time that a compartment was opened, or a take medication alert was generated. The display also indicates the number of pills, and the compartment corresponding to the particular scheduled medication. If a medication signal was generated, and the appropriate compartment was not opened in a predetermined time period (e.g. 10 or 1 hour), the LCD will also display a "missed pill" indication, corresponding to that scheduled medication alert. If a number of medication alerts or unscheduled openings of a drawer occurred simultaneously, each of the medication signals will be displayed sequentially, through sequential actuation of the "LAST" button 9, while the time indication of the time of each of these events remains the same.

Actuation of the "LAST" button 9 during this routine will continue to sequence through each of the last occurrences during the previous 24 hours, displaying each occurrence after each actuation of the "LAST" button 9, until the entire previous 24 hours of activity of the device has been replayed. Once the full 24 hours has been displayed, actuation of the "LAST" button 9 will take the flow of the microprocessor 1 back to that location in its operation prior to the initial selection of the last routine, or return to "TIME-OF-DAY?".

During the "LAST" routine, actuation of the "NEXT" button 10, the "CHECK" button 11 or the "SET" button 12 will have no effect on the operation of the microprocessor 1 or the display 2. Actuation of the "YES/OKAY" button 13 or the "NO" button 14 or the opening of one of the compartments or the occurrence of a medication alert time will cause the last routine to terminate and the microprocessor to return to that location in its operation prior to the initial selection of the last routine, or return to "Time-of-Day?".

FIG. 8 illustrates the "NEXT" routine, which is similar to the "LAST" routine above. In this mode, each designated medication time for each compartment, with each quantity of medication, over the next 24 hours is displayed through sequential actuation of the "NEXT" button 10. Once all of the scheduled times have been displayed for the next 24 hour time period, the microprocessor 1 is sequenced back to that location in its operation prior to the initial selection of the next routine, or returned to "Time-of-Day?". The "LAST" 9, "CHECK" 11 and "SET" 12 buttons are rendered ineffective during the "NEXT" routine. Actuation of the "YES/OKAY" 13 or "NO" 14 button or the opening of one of the compartments or the occurrence of an medication alert time will cause the next routine to terminate and the microprocessor 1 to return to that location in its operation prior to the initial selection of the next routine, or return to "Time-of-Day?".

The provision of these two routines allows the user or other monitoring personnel to prospectively view the programed medication times for the next 24 hour period and to retrospectively view the medication administered or missed during the last 24 hours. The device is therefore not limited only to medication reminding but also allows for medication monitoring. Through the extension of the internal RAM storage of the microprocessor 1, information covering a time period greater than 24 hours can be stored. An optional data port 33 can be provided to supply this prospective and/or retrospective information to a external device such as a printer, a data storage medium, a computer or other device.

Figure 10:
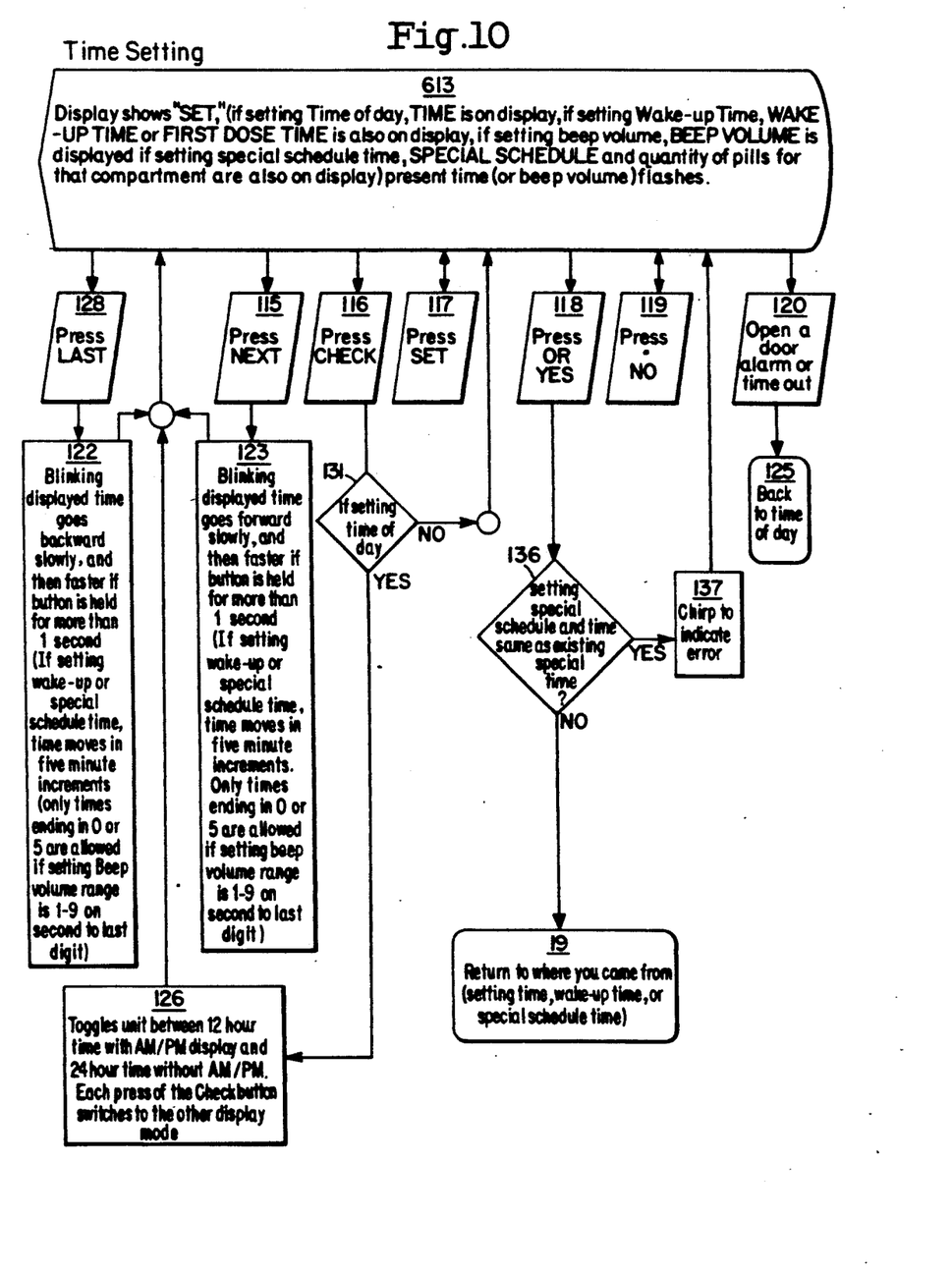

The check First-Dose-Time routine, FIG. 9, displays the preset First-Dose-Time and allows to be changed by entering the time setting routine block 921, FIG. 10, by actuation of the "SET" button 12. From this routine, the medication alert schedule can also be viewed by actuation of the "CHECK" button 11. The Processor will then proceed with the check schedule routine, FIG. 13.

FIG. 10 illustrates the time setting operation of the microprocessor 1. This routine is used to set the time of day, to set the First Dose Time, and to set special scheduled medication times. Special schedule medication times are those which must be set at a particular time, for which the built in time increments such as "every-four-hours" will not provide. Therefore these times need to be specifically input. This routine is entered from each of these functions as appropriate to the performance of that function. When in the time setting routine, actuation of the "NEXT" button 10 increments the time and actuation of the "LAST" button decrements the time.

The unscheduled pill routine, FIG. 11, is entered when a drawer is opened at a time other then a scheduled medication time. This routine instructs the display 2 to display the appropriate quantity of pills for the drawer that was opened. The user is prompted via an audible "chirp" and the query "UNSCHEDULED PILL?" to indicate whether or not an unscheduled medication is being taken. If the user actuates the "YES/OKAY" button 13 the microprocessor 1 will record that an unscheduled medication was taken. If the user does not respond within a predetermined period of time, or if the user actuates the "NO" button 14, the microprocessor will assume that no medication was taken. Each incidence of unscheduled medication is recorded for later review and display as described above in the "NEXT" and "LAST" review routines.

The alarm mode block 617 of FIG. 12 is entered when the scheduled time and the time of day correspond. If the drawer of the compartment containing the correct pills is opened, the alarm condition is satisfied. If more than one compartment needs to be accessed, all compartments must be opened in order to satisfy the alarm condition. The user is prompted as to which drawers must be opened by the activation of the LED corresponding to the compartment and the indication of pill quantity above the compartment. If a wrong drawer is opened, the unit chirps and queries "UNSCHEDULED PILL?" to help prevent improper medication at an alarm time.

The user is also prompted if medication has been missed and can then view this missed medication through actuation of the "LAST" button 9 and can view the next medication by actuation of the "NEXT" button 10. The user can then decide to take the missed medication or not and so inform the microprocessor 1 by actuation of the "YES/OKAY" button 13 or "NO" button 14.

Figure 13:
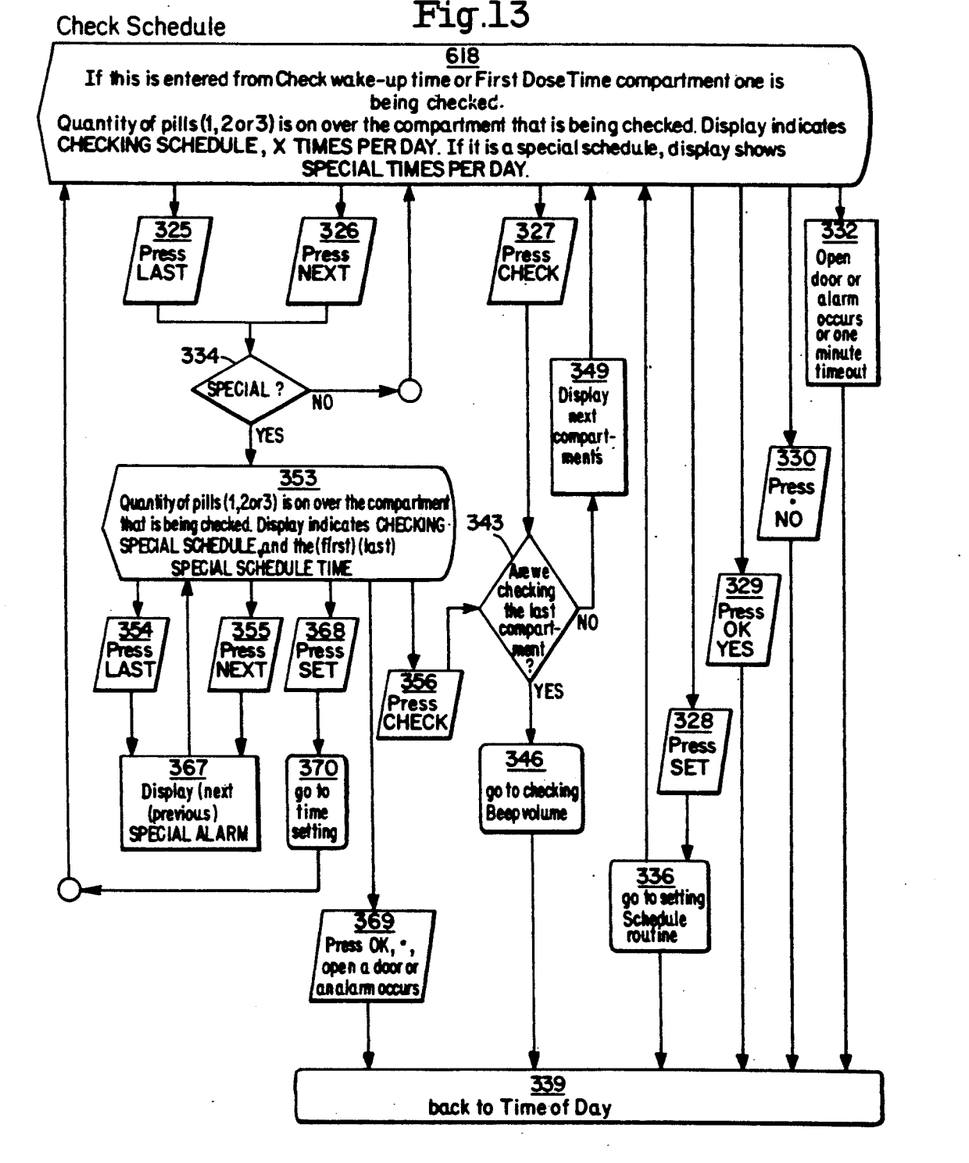

The check schedule routine FIG. 13 allows the user to sequentially view the scheduled medication times by actuation of the "LAST" and "NEXT" keys. The time of medication is displayed, as well as the quantity and the LED of the appropriate compartment is activated.

Figure 14:
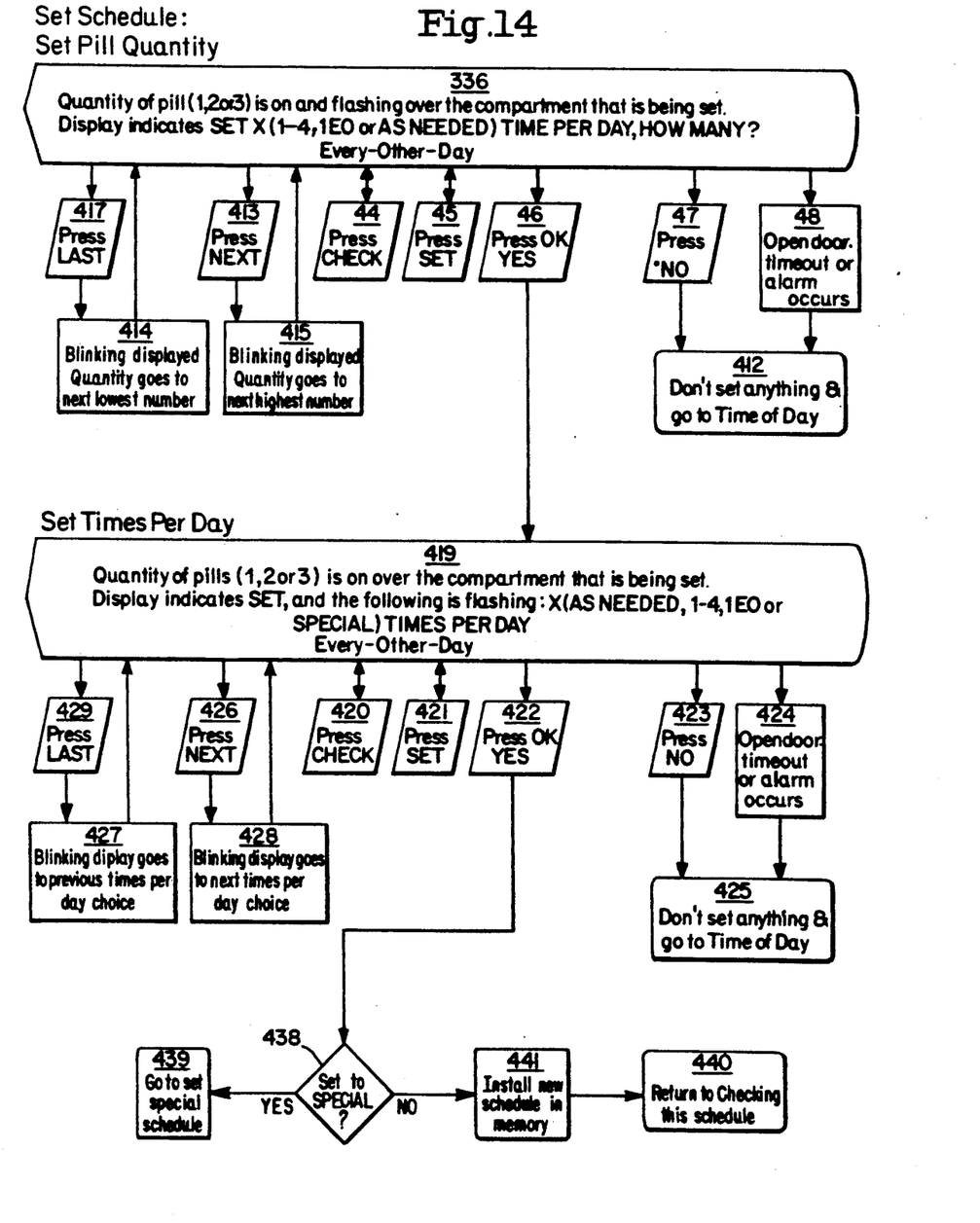

FIG. 14 illustrates the logical operation of selecting the quantity of pills to be taken and selecting one of the preset, i.e. non-special, times per day settings for medication alerts.

Figure 15:
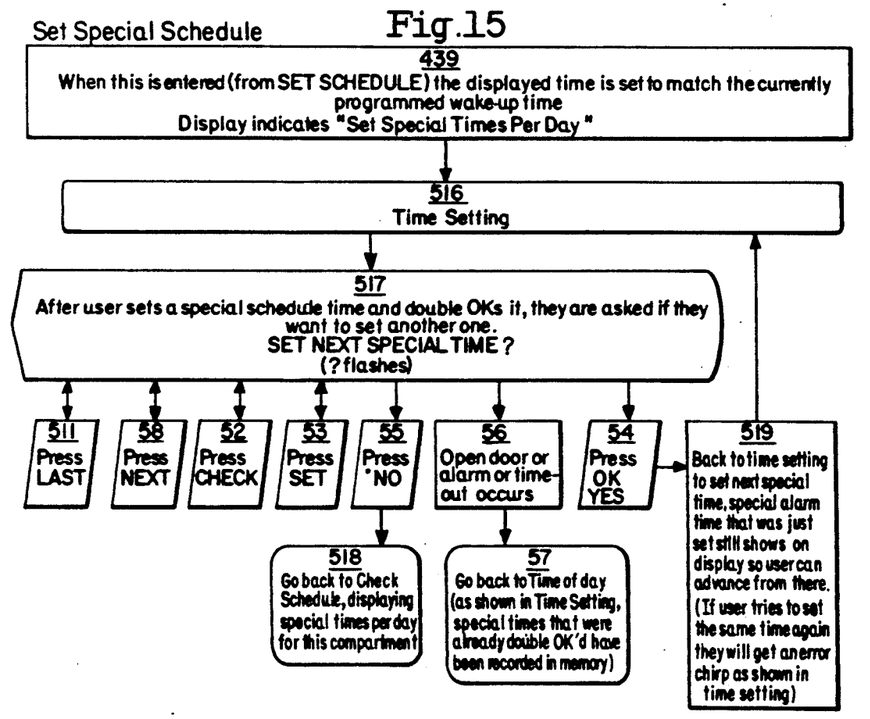
Figure 16:
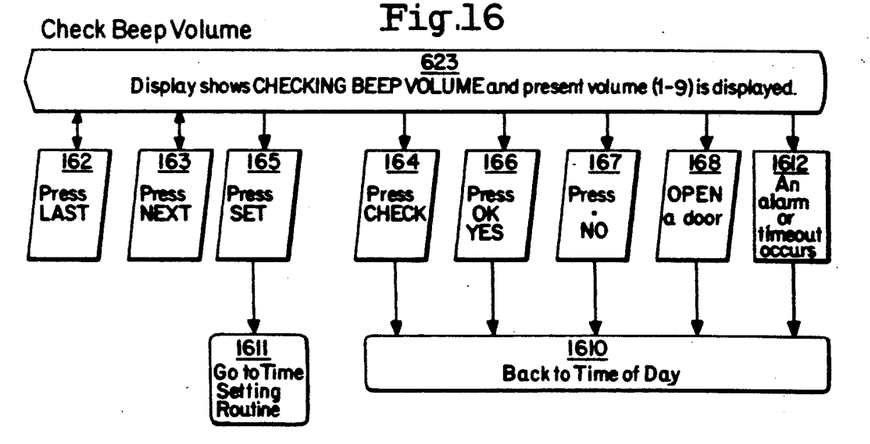

The set special schedule routine, FIG. 15 is a special case of the time setting routine, which, when entered allows the user to establish a non-standard medication alert time. Once this routine is entered, the patient or user can enter the specific times of day that medication should be taken allowing greater flexibility than simply choosing one of the preset standards of "three-times-daily" etc.

It is to be understood that the above embodiment and description is exemplative of one preferred embodiment of a medical monitor according to the inventive concept of the present invention. The disclosure is to be interpreted in an illustrative and not a limiting sense. The scope of the invention is defined in the following claims.

What is claimed is:

1. A device for monitoring the medication of an individual patient, comprising:
    a casing,
    a display means for displaying messages,
    a plurality of accessible medication compartments in said casing,
    control means for storing a schedule of medication alert signals, for providing timing signals and for controlling said display means,
    means responsive to said control means for producing medication alert signals, and
    a plurality of user actuatable input means carried by said casing and connected to said control means for programming said control means,
    said display means having a substantially continuous display area extending closely adjacent to each of said compartments,
    wherein said control means includes means for displaying information on said display means at a location adjacent to one or more compartments.

2. A device as defined in claim 1, comprising:
    means supporting said compartments to permit each one of them to be opened and closed, said display means being a permanent fixed part of said device and is visible to the user of the device concurrently with the contents of one of said compartments when such compartment is open.

3. A device as defined in claim 1, comprising:
    said control means including means for providing at least one special schedule for at least one of said compartments, for giving a medication alert signal according to said special schedule and for designating the compartment as to which the medication alert signal, given in accordance with said special schedule, applies.

4. A device as defined in claim 1, comprising:
    said casing having a top surface, and having a bottom surface, said containers being adjacent each other and each having a front surface, the front surfaces of said containers taken together forming at least part of a sidewall that connects said top and bottom surfaces.

5. A device as defined in claim 1, in which said casing has a top side, said compartments having open and closed positions, said display means and said input means forming a part of said top side, said compartments being in said casing and under said top side when closed.

6. A device as defined in claim 1, comprising:
    means for supporting said compartments to permit them to be opened and closed, and
    each of said compartments having switch means to sense a movement of such compartment and for giving a signal to said control means,
    said control means terminating a medication alert signal in response to a signal from said switch means.

7. A device as defined in claim 1 in which said control means comprises a microprocessor.

8. A device as defined in claim 1, comprising:
    said control means including memory means for storing said schedule,
    means supporting said compartments to allow them to be opened and closed,
    switch means for detecting movement of said compartments, and
    means for correlating the time of operation of said switch means with said schedule, and giving an indication on said display means in accordance with such correlation or lack thereof.

9. A device according to claim 1, comprising:
    said control means including means which, when said schedule calls for a medication alert signal, said means for producing medication alert signals will produce a medication alert signal and cause said display to display the amount of medication to be taken on a portion of said area that is closely adjacent to the compartment which contains the medication which is to be taken in response to the medication alert signal.

10. A device according to claim 1, in which said input means includes means for providing a medication alert schedule to said control means.

11. A device as defined in claim 1 in which said input means includes means for providing messages to said control means for display on said display means.

12. A device as defined in claim 1 in which said input means includes means for instructing said control means to display said schedule, including prospective and retrospective versions of said schedule.

13. A device as defined in claim 1, comprising:
    switch means associated with each of said compartments for sensing the movements of said compartments, said switch means providing a compartment movement signal to said control means,
    said control means including a random access memory for storing the occurrence of selected signals relating to said schedule and the operations of said switch means, and said input means including mans for directing said control means to cause said display means to display selected information.

14. A device as defined in claim 1 in which said input means includes means to suspend a selected medication alert signal while giving other medication alert signals.

15. A device as defined in claim 1, comprising:
a memory having a missed medication routine stored therein,
said control means including means for activating said display means to display said missed medication routine in the event that the user does not access the proper compartment in response to a medication alert signal.

16. A device as defined in claim 15, comprising:
said input means and said control means comprising means for monitoring the medication taken and the medication missed over a period of time and for displaying the information so monitored.

17. A device as defined in claim 1, comprising:
said control means including a random access memory,
said control means including means that provides said medication alert signals in audible form,
manually operable means for selecting the amplitude of said audible signal and for storing said amplitude in said memory, and
means for displaying said selected amplitude,
said control means including means for causing subsequent audible signals to be given at the selected amplitude.

18. A device as defined in claim 1, in which said control means includes a memory for storing a plurality of routines for taking medicine, said input means including means for selecting one of said routines.

19. A device as defined in claim 18, in which said control means includes means for displaying the selected routine on said display means.

* * * * *